United States Patent
Verma et al.

(10) Patent No.: US 6,322,811 B1
(45) Date of Patent: Nov. 27, 2001

(54) ALKYLENE OXIDE POLYMER COMPOSITIONS

(75) Inventors: Surendra Kumar Verma, Charleston; Michael Scott Jarrell, South Charleston, both of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/601,633

(22) PCT Filed: Feb. 5, 1999

(86) PCT No.: PCT/US99/02526

§ 371 Date: Sep. 25, 2000

§ 102(e) Date: Sep. 25, 2000

(87) PCT Pub. No.: WO99/40156

PCT Pub. Date: Aug. 12, 1999

Related U.S. Application Data

(60) Provisional application No. 60/073,872, filed on Feb. 6, 1998.

(51) Int. Cl.[7] ............................. A61K 9/48; B32B 15/02
(52) U.S. Cl. .................. 424/451; 428/402; 428/402.21; 424/464; 424/485; 424/486; 424/488; 424/489
(58) Field of Search ............................. 428/402, 402.21; 424/451, 464, 485, 486, 488, 489

(56) References Cited

U.S. PATENT DOCUMENTS

| | | | |
|---|---|---|---|
| 3,164,560 | 1/1965 | Suter | 260/6 |
| 3,328,916 | 7/1967 | Okita et al. | 47/56 |
| 3,561,187 | 2/1971 | Rohnert et al. | 53/28 |
| 3,683,583 | 8/1972 | Cochran et al. | 53/28 |
| 3,772,849 | 11/1973 | Tobin, Jr. et al. | 53/180 |
| 3,893,258 | 7/1975 | Compton et al. | 47/58 |
| 3,941,865 | 3/1976 | Miller et al. | 264/95 |
| 3,991,517 | 11/1976 | Lewis | 47/57.6 |
| 3,999,358 | 12/1976 | Lewis | 53/28 |
| 4,001,211 | 1/1977 | Sarkar | 536/84 |
| 4,026,986 | 5/1977 | Christen et al. | 264/301 |
| 4,028,024 | 6/1977 | Moreland | 425/133.1 |
| 4,609,403 | 9/1986 | Wittwer et al. | 106/122 |
| 4,738,724 | 4/1988 | Wittwer et al. | 106/213 |
| 4,774,092 | 9/1988 | Hamilton | 424/453 |
| 4,851,394 | 7/1989 | Kubodera | 514/54 |
| 4,883,660 | 11/1989 | Blackman et al. | 424/78 |
| 5,342,626 | 8/1994 | Winston et al. | 424/461 |
| 5,405,564 | 4/1995 | Stepto et al. | 264/115 |
| 5,431,917 | 7/1995 | Yamamoto et al. | 424/451 |
| 5,614,578 | 3/1997 | Dong et al. | 524/377 |
| 5,660,859 | 8/1997 | Cody | 424/451 |
| 5,756,036 | 5/1998 | Grosswald et al. | 264/304 |
| 5,965,150 | 10/1999 | Wada et al. | 424/408 |

FOREIGN PATENT DOCUMENTS

| | | |
|---|---|---|
| 9209274 | 11/1991 | (WO) |
| WO 9613248 | 10/1995 | (WO) |
| 9735537 | 3/1997 | (WO) |
| WO 9827151 | 12/1997 | (WO) |
| WO 9907347 | 5/1998 | (WO) |

OTHER PUBLICATIONS

Scientific Status Summary, Edible and Biodegradable Polymer Films: Challenges and Opportunities, vol. 51, No. 2, Feb., 1997, Krochta et al. pp. 61–74.

International Journal of Food Science and Technology (1990) 28, 527–537, Preparation of transparent pea protein gels: a comparison of isolation procedures, Bacon et al.

Technology News Degradables, Moldable, Water–Soluble Starch–Based Resin Arrives, Plas. Tech. 37, No. 10, Sep. 1991, pp 19–23.

*Primary Examiner*—Samuel A. Acquah

(57) ABSTRACT

Alkylene oxide polymer compositions having particular molecular weight distributions are disclosed. As a result of the molecular weight distributions, the disclosed alkylene oxide polymer compositions are suitable, among other things, for the manufacture of films, e.g., for use in manufacturing soft gel capsules. Capsules made from the disclosed alkylene oxide polymer compositions can provide enhanced resistance to crosslinking often caused by liquid filling materials, e.g., polyethylene glycol, used in gelatin capsule manufacture.

16 Claims, No Drawings

ALKYLENE OXIDE POLYMER COMPOSITIONS

This appln is a 371 of PCT/US99/02526 filed Feb. 5, 1999 which claim benefit of provisional No. 60/073,872 filed Feb. 6, 1998.

FIELD OF THE INVENTION

The present invention relates to alkylene oxide polymer compositions. More specifically, the present invention relates to alkylene oxide polymer compositions having molecular weight distributions suitable for the manufacture of films, e.g., water soluble, flexible films for use as soft gel capsules.

BACKGROUND OF THE INVENTION

Gelatin is a protein material produced by hydrolysis of collagen from animal bones and connective tissues. Gelatin has served as an encapsulating material, a coating for pills, an emulsifying agent, a coating for photographic materials, a bacterial culture medium, a component of printers' rollers and hectograph plates, an ingredient of popular desserts, and for many other widely varied uses.

One common use for gelatin is in the manufacture of soft gel capsules for the delivery of active ingredients. Although gelatin is generally strong and tough, its extensibility and flexibility are generally low. In addition, since gelatin is derived from animal sources, there are often inconsistencies in product quality from batch to batch. The physical and chemical properties of gelatin are a function of the source of the collagen, method of manufacturing, conditions during extraction and concentration, thermal history, pH and the chemical nature of impurities and additives. Moreover, during storage, gelatin often undergoes a crosslinking reaction which in turn changes the dissolution character and the drug bio-availability characteristics. This shortens the useful life of the gelatin. Thus, mechanical failures of gelatin soft gel capsules are often encountered. Additionally, the use of animal derived materials, such as gelatin, has come under regulatory review due to concerns regarding the transmission of animal based illness.

Accordingly, new materials are desired which can function as replacements for gelatin, particularly gelatin based films useful for manufacturing soft gel capsules and the like.

SUMMARY OF THE INVENTION

By the present invention, problems commonly associated with the use of gelatin in manufacturing films, used for example in manufacturing soft gel capsules, have been solved. More specifically, films manufactured using the polymer compositions of the present invention can have enhanced stability, processability and physical and chemical properties as compared to films made from gelatin.

In accordance with the present invention, alkylene oxide polymer compositions having certain molecular weight distributions are provided. Advantageously, the polymer compositions of the present invention are water soluble. However, quite surprisingly, films made from the compositions of the present invention are substantially insoluble in aqueous polyethylene glycol solutions, a liquid often used as a physiologically acceptable carrier, when such solutions contain about 25 wt. % water or less. As a result of the high water tolerance of the films, capsules made from these films can accommodate increased amounts of active ingredients, e.g., acetaminophen, in the capsule. In accordance with the present invention, enhancements in the concentration of the active ingredients in the fill can often be up to 30 percent or more as compared to a comparable gelatin capsule.

DETAILED DESCRIPTION OF THE INVENTION

The alkylene oxide polymers of the present invention are prepared from alkylene oxide monomers containing from about 1 to 5 carbon atoms per molecule, e.g., ethylene oxide or propylene oxide, as well as copolymers and derivatives thereof. Alkylene oxide monomers suitable for use as starting materials are commercially available.

Preferably, the alkylene oxide polymers of the present invention comprise ethylene oxide polymers. The ethylene oxide polymers include, for example, homopolymers of ethylene oxide and copolymers of ethylene oxide with one or more polymerizable comonomers. The particular comonomer is not critical to the present invention and may contain hydrocarbon substituents, such as, for example, alkyl, cycloalkyl, aromatic, alkene (also referred to as alkylene) or branched alkyl or alkene groups; provided, however, that the water solubility or water-dispersibility is maintained. Further details concerning the preparation of ethylene oxide polymers is known in the art. See for example, U.S. Pat. No. 2,969,403 issued to Helmut et al., U.S. Pat. No. 3,037,943 issued to Bailey et al., U.S. Pat. No. 3,167,519 issued to Bailey et al., U.S. Pat. No. 4,193,892, issued to Goeke et al. and U.S. Pat. No. 4,267,309 issued to Goeke et al.

The desired molecular weight distribution of the alkylene oxide polymers of the present invention can be obtained by polymerizing the alkylene oxide monomers directly or by blending alkylene oxide polymers having different molecular weight ranges. For polymers having a molecular weight of less than 50,000 grams per gram mole ("g/gmol"), as used herein, the term "molecular weight" means number average molecular weight (sometimes referred to herein as "$M_n$"). For polymers having a molecular weight of 50,000 g/gmol or higher, as used herein, the term "molecular weight" means weight average molecular weight (sometimes referred to as "$M_w$"). Techniques for determining the average molecular weight are known to those skilled in the art. A suitable technique to determine number average molecular weight is by end group titration and a suitable technique to determine the weight average molecular weight is by light scattering.

Often in the art, alkylene oxide polymers having molecular weights of about 50,000 and higher are referred to as polyalkylene oxides, e.g., polyethylene oxide, and alkylene oxide polymers having molecular weights of less than about 50,000 are referred to as polyalkylene glycols, e.g., polyethylene glycol. Polyalkylene oxides and polyalkylene glycols are commercially available, for example, from Union Carbide Corporation, Danbury, Conn., under the tradenames POLYOX® Water Soluble Resins and CARBOWAX® polyethylene glycols (PEG), respectively. Preferably, various polyalkylene glycols and polyalkylene oxides are blended in appropriate proportions to achieve the desired molecular weight distribution of the alkylene oxide polymer compositions of the present invention.

In accordance with the present invention, the alkylene oxide polymer compositions typically comprise from 1 to about 25 wt. %, more typically from 1 to about 19 wt. %, preferably from about 2 to 19 wt. %, and more preferably from about 3 to 18 wt. % of alkylene oxide polymer having a molecular weight of about 100 to 2,000 g/gmol, typically 100 to 1,000 g/gmol.

The alkylene oxide polymer compositions further typically comprise from about 10 to 60 wt. %, more typically from about 10 to 50 wt. %, preferably from about 20 to 45 wt. % and more preferably from about 25 to 35 wt. % of alkylene oxide polymer having a molecular weight of from about 1,000 to 50,000 g/gmol, typically about 2000 to 50,000 g/gmol and preferably from about 1,000 to 25,000 g/gmol.

Additionally, the alkylene oxide polymer compositions of the present invention typically comprise from about 25 to 89 wt. %, preferably from about 30 to 75 wt. %, more preferably from about 35 to 70 wt. % and most preferably from about 45 to 65 wt. % of alkylene oxide polymer having a molecular weight of from about 50,000 to 10,000,000 g/gmol, preferably from about 100,000 to 4,000,000 g/gmol.

Unless otherwise indicated, the weight percentages of the various molecular weight fractions are based on the total weight of the alkylene oxide polymer composition, e.g., including water, other polymers and additives as hereinafter described. The alkylene oxide polymer compositions of the present invention may comprise one or more alkylene oxide polymers within each molecular weight range. For instance, in one aspect of the invention, the alkylene oxide polymer composition comprises an alkylene oxide polymer having a molecular weight of 1,450 g/gmol and an alkylene oxide polymer having a molecular weight of about 8,000 g/gmol, both of which are within the more broadly stated range of about 1,000 to 50,000 g/gmol.

The alkylene oxide polymer compositions of the present invention may comprise additional polymers in order to achieve desired properties. Such other polymers include, for example, naturally occurring and synthetic neutral, cationic, anionic and amphoteric polymers, e.g., polysaccharides and derivatives thereof, hyaluronic acid, other polyalkylene oxides, linked or cross linked polyalkylene oxides with linkers like epoxides, polyvinyl pyrrolidones, polycaprolactones, polyvinyl acetates and polycarboxylic acids, copolymers of alkylene oxide, acrylic acid and vinyl acetate. The polysaccharides include naturally occurring, biosynthesized and derivatized carbohydrate polymers and mixtures thereof. Such materials encompass high molecular weight polymers composed of monosaccharide units joined by glycosidic bonds. These materials may include, for example, the entire starch and cellulose families; pectin, chitosan; chitin; the seaweed products such as agar and carrageenan; alginate; the natural gums such as guar, arabic and tragacanth; bio-derived gums such as xanthan; and the like. Common polysaccharides include cellulosics conventionally employed for the preparation of cellulose ethers, such as, for example, chemical cotton, cotton linters, wood pulp, alkali cellulose and the like. Such materials are commercially available. The molecular weight of the polysaccharides typically ranges from about 10,000 to 2,000,000 grams per gram mole. Preferably, the polysaccharides are etherified by reacting the polysaccharide with an alkylene oxide, e.g., ethylene oxide, propylene oxide or butylene oxide or otherwise derivatized by techniques known to those skilled in the art.

When such other polymers are used in the compositions of the present invention, they are typically present in amounts of from 1 to about 20 wt. %, and more typically from about 2 to 15 wt. % based on the total weight of the alkylene oxide polymer composition.

Preferably, the alkylene oxide polymer compositions of the present invention comprise water in an amount of from 1 to about 20 wt. %, more preferably from 1 to about 10 wt. % and most preferably from about 3 to 8 wt. % based on the total weight of the alkylene oxide polymer composition. Preferably, water is present in an amount effective to equilibrate with the amount of moisture in the air or other environment in which the compositions are stored, particularly when the compositions are used to manufacture films, e.g., gel capsules, as hereinafter described.

Other additives may be present in the alkylene oxide polymer compositions of the present invention in amounts from about 5 parts per million by weight ("ppmw") to about 15 wt. % often about 10 wt. % or less, based on the total weight of the composition. Typically, other additives comprise for example, preservatives, antioxidants, colorants, opaquing agents and the like.

In one aspect of the invention, the alkylene oxide compositions of the present invention contain minor amounts, e.g., less than about 20 wt. % based on the total weight of the composition, of gelatin. More preferably, there is a substantial absence, e.g., less than about 5 wt. %, preferably less than about 1 wt. % based on the total weight of the composition, of gelatin.

The alkylene oxide compositions of the present invention may be provided in any desired form. Typical forms include, for example, liquids, small particles, e.g., 0.001 to about 100 microns, large particles or granules, e.g., about 1 to 10 millimeters ("mm"), extrudates, tablets, films and capsules.

The alkylene oxide polymer compositions of the present invention are particularly suitable for manufacturing films. Typically, prior to making the films, polymers having the desired molecular weights are first uniformly blended along with water in a conventional mixer such as a V blender, Hobart mixer, or ball mill, e.g., for about 60 minutes. A preferred composition is comprised of 5.4 wt. % of CARBOWAX® PEG 300 ($M_w$=300 g/gmol), 8.1 wt. % of CARBOWAX® PEG 1450 ($M_w$=1450), 27 wt. % of CARBOWAX® PEG 8000 ($M_w$=8000), 54 wt. % of POLYOX® WSR N-750 ($M_w$=300,000) and 5.5 wt. % water. Details concerning the manufacture of films comprising the alkylene oxide polymers of the present invention are known to those skilled in the art.

Preferably, films made from the alkylene oxide polymer compositions of the present invention have thicknesses of from about 0.05 to 1.0 mm and preferably from about 0.1 to 0.5 mm. Typically, the films are flexible, i.e., not rigid, and are water soluble, disperse or disintegrate rapidly in water. As used herein, the term "water soluble" means that at least one gram and preferably two grams of the alkylene oxide polymer composition are soluble in 100 grams of distilled water at 25° C. and one atmosphere.

Preferably, the films made from the alkylene oxide polymer compositions of the present invention have desirable properties in terms of flexibility, toughness, uniformity and clarity. Typically, the mechanical properties of the films prepared by the alkylene oxide polymer compositions of the present invention have the following mechanical properties. The tensile strength of extruded and thermal pressed films, as measured in accordance with ASTM Method 412-68, is at least about 200 psi or more with an elongation of at least about 50%. Normally, the air blown films have about 20% lower tensile strength. Furthermore, the films are preferably sealable. That is, the films should be able to seal onto themselves with the help of elevated temperature, pressure, or both, with or without the help of a dilute aqueous solution of one of the ingredients of the film. Further details concerning the sealing of ethylene oxide polymer films are known in the art. See for example, U.S. Pat. No. 3,999,358 issued to Lewis, et al.

Quite surprisingly, the alkylene oxide polymer compositions of the present invention are substantially insoluble in polyalkylene glycols and aqueous polyethylene glycol solutions (molecular weight equal to 400 g/gmol) containing up to about 25 wt. % water. As used herein, the term "substantially insoluble" means that less than about 5 wt. %, preferably less than about 3 wt. % and more preferably less than about 1 wt. % of the polymer dissolves in the solution at 25° C. and one atmosphere over a time period of 10 minutes. This unexpected property provides a solution to the problem of mechanical failures associated with gelatin soft gel capsules where the liquids used inside the capsules often adversely affect the integrity of the capsule walls. More specifically, polyalkylene glycols, e.g., polyethylene glycol, are often used as the liquid filling material in soft gel capsules because they are physiologically acceptable carriers. Polyethylene glycol has a high infinity for the gelatin capsules and softeners often used in preparing soft shell gelatin capsules. As a result, the gelatin capsules can undergo a crosslinking reaction which changes the dissolution character and drug bio-availability characteristics.

Thus, a preferred use for the alkylene oxide polymer compositions of the present invention is in the manufacture of soft gel capsules. Quite advantageously, the alkylene oxide compositions of the present invention can replace gelatin in the manufacture of soft shell capsules. In general, the soft shell capsules can be prepared by a rotary die process in which they are formed, filled, and sealed in a single operation. They are filled with a solution or suspension of drug or die in liquids that will not solubilize the shell.

The compositions of the present invention can also be used to manufacture hard shell capsules which are generally rigid. The hard shell capsules comprise two, fitted cap and body pieces. The rigidity of the capsule can be increased by increasing the amount of the high molecular weight polymer fractions and/or decreasing the low molecular weight polymer fractions. They can be made by a punch and die operation that is carried out at above the softening temperature of the polymer, e.g., 50 to 80° C.

In general, the capsules of the present invention, both hard shell and soft gel, comprise a continuous, flexible wall having an outer surface and an inner surface. The wall is comprised of a film made from the alkylene oxide polymer compositions of the present invention. The inner surface of the capsule at least partially surrounds the inner space of the capsule.

Further details concerning the manufacture of gel capsules and appropriate apparatus useful in manufacturing such capsules are known in the art, such as described in U.S. Pat. No. 4,028,024 issued to Moreland.

The size of the capsules can be determined by those skilled in the art depending upon the intended use. For example, capsules for oral drug delivery for humans will typically have a size ranging from about 1 mm to 10 mm. In contrast, capsules for oral drug delivery for animals may be significantly larger, e.g., about 10 mm to 30 mm. Capsules used for other purposes, such as, for example, in the manufacture of paint balls may be relatively large, whereas capsules used to contain ink or other fluids may be extremely small. Thus, typically the size of the capsules will range from about 1 mm to 50 mm. In the case of non-spherical capsules, e.g., elliptically shaped capsules, the above mentioned diameter is made with reference to the largest dimension perpendicular to the longitudinal axis.

The capsules of the present invention may or may not contain a filling or material within the inner space of the capsule. When the capsules contain a filling, such filling can be a liquid, gas, semi-solid, solid or gel. The particular form of the filling is not critical to the present invention.

Often, liquid fillings are employed in the capsules of the present invention. Preferably, the liquid used as the filling material does not adversely affect the integrity of the capsule wall. More specifically, it is preferred that the liquid does not promote the dissolution of the capsule wall or cause the capsule wall to crosslink over time. Typically, the interior space of the capsule will be at least 10 percent by volume filled with liquid, preferably at least 25 percent, more preferably at least 50 percent and most preferably at least 75 volume percent filled.

Those skilled in the art will recognize that the capsules of the present invention will have a variety of industrial and personal care uses. For instance, the capsules can be used for the oral delivery of pharmaceutically active agents to humans and animals. In addition, the capsules can be used in personal care applications, e.g., hair care and skin care formulations, to deliver oils, vitamins, proteins, polymers and other personal care ingredients. The capsules can also be used, for example, to provide bath oil beads, fragrances and time released ingredients. Further, the capsules can be used in the manufacture of paint balls and other recreational products. Moreover, the capsules can be employed in a variety of industrial uses, such as, for example, in the delivery of inks, catalysts, initiators, enzymes, and the like. The amount of the particular active ingredient utilized depends on the particular end use. Typically, the amount of active ingredient will range from about 0.01 to 99 wt. % based on the total weight of the filling material, e.g., liquid and active. As used herein, the term "active ingredient" means the ingredient or ingredients introduced into the capsule to achieve the desired effect upon delivery. Whether such effect is pharmacological, chemical, cosmetic, physical or otherwise is not critical to the present invention. Further details concerning the selection and amounts of the appropriate filling materials and active ingredients can be determined by those skilled in the art.

One preferred end use for the capsules of the present invention is for the delivery of active ingredients in pharmaceutical and personal care applications. For such applications, the liquid material comprises a physiologically acceptable carrier, preferably a polyalkylene glycol, more preferably polyethylene glycol having a weight average molecular weight of about 100 to 500, preferably about 400 g/gmol. More preferably, the filling material comprises an aqueous, polyalkylene glycol solution comprising from about 1 to 30 wt. %, typically from about 5 to 25 wt. %, preferably from about 10 to 25 wt. % and more preferably from about 15 to 25 wt. % water, based on the total weight of the liquid, e.g., polyalkylene glycol plus water.

Typical actives for personal care applications, i.e., both pharmaceutical and cosmetic, include but are not limited to spermicides, virucides, analgesics, anesthetics, antibiotic agents, antibacterial agents, antiseptic agents, vitamins, corticosteriods, antifungal agents, vasodilators, hormones, antihistamines, autacoids, decongestants, bronchodilators and other antiasthmatic agents, beta-blockers, anti-nauseants, antiemetics, anticonvulsants, kerolytic agents, anti-diarrhea agents, anti-alopecia agents, anti-inflammatory agents, exfoliating agents, sunscreens, anti-oxidants, enzymes, anti-infection agents. Typical pharmaceutically active ingredients suitable for use in the invention include acetaminophen, famotidine, chlorpheniramine, pseudoephedrine, dectromethorphan, diphenhydramine, brompheniramine, phenylpropanolamine, clemastine, terfenadine, astemizole, pharmaceutically acceptable salts thereof and mixtures thereof.

Other components of the liquid filling material can be determined by those skilled in the art and include materials, such as for example, solvents, diluents and adjuvants such as, for example, ethyl alcohol, isopropyl alcohol, higher alcohols, glycerine, propylene glycol, sorbitol, preservatives, surfactants, menthol, eucalyptus oil, other essential oils, fragrances, viscosity adjusters, and the like.

The concentration of the active ingredient in the capsule is, of course, dependent on the particular end use and the active agent, which can be determined by those skilled in the art. For example, the pharmaceutically active ingredients are usually present in the capsule in a therapeutically effective amount which produces the desired therapeutic response upon administration. In determining such amounts, the particular compound being administered, the bio-availability characteristics of the compound, the dose regiment, the age and weight of the patient, and other factors must be considered.

The following Examples are provided for illustrative purposes and are not intended to limit the scope of the claims which follow. The concentrations of ingredients are provided in weight percent unless otherwise indicated.

The designations and abbreviations used in the Examples are defined as follows:

| | |
|---|---|
| POLYOX ® WSR N 750 | An ethylene oxide polymer having a molecular weight of about 300,000 g/gmol, available from Union Carbide Corporation, Danbury, CT. |
| POLYOX ® WSR N 10 | An ethylene oxide polymer having a molecular weight of about 100,000 g/gmol, available from Union Carbide Corporation, Danbury, CT. |
| CARBOWAX ® PEG Compound 20M | An epoxide linked polyethylene glycol having a molecular weight of about 18,000 g/gmol, available from Union Carbide Corporation, Danbury, CT. |
| CARBOWAX ® PEG 8000 | A polyethylene glycol having a molecular weight of about 8,000 g/gmol, available from Union Carbide Corporation, Danbury, CT. |
| CARBOWAX ® MPEG 5000 | A methoxy polyethylene glycol having a molecular weight of about 5,000 g/gmol, available from Union Carbide Corporation, Danbury, CT. |
| CARBOWAX ® PEG 1450 | A polyethylene glycol having a molecular weight of about 1450 g/gmol, available from Union Carbide Corporation, Danbury, CT. |
| CARBOWAX ® PEG 400 | A polyethylene glycol having a molecular weight of about 400 g/gmol, available from Union Carbide Corporation, Danbury, CT. |
| CARBOWAX ® PEG 300 | A polyethylene glycol having a molecular weight of about 300 g/gmol, available from Union Carbide Corporation, Danbury, CT. |
| CELLOSIZE ® HEC QP-40 | Hydroxyethyl cellulose having a molecular weight of about 120,000 g/gmol, available from Union Carbide Corporation, Danbury, CT. |
| TONE ® Polymer P-767 | A polycaprolactone resin having a molecular weight of about 35,000 to 55,000 g/gmol, available from Union Carbide Corporation, Danbury, CT. |
| PVAc GB 101 | A vinyl acetate polymer having a molecular weight of about 40,000 g/gmol, available from Union Carbide Corporation, Danbury, CT. |
| PVP (Polyvinylpyrrolidone) | A 1-ethynyl-2-pyrrolidinone polymer |

The following test procedures define the performance tests used in the evaluation.

The tensile strength measurements were conducted on an Instron Extensometer employing ASTM Method D 412-68. Film dissolution studies were conducted by a visual and a gel permeation chromatographic (GPC) method. A piece of the film with known weight (0.05 to 0.5 gram) was added to 10 grams of water or an aqueous PEG solution. The time it took to dissolve the film was recorded. If the film did not dissolve in over 42 hours, the observation was stopped. The liquid phase was sampled periodically and analyzed by GPC to detect the presence of components of the film in the solution.

Films were viewed under Scanning Electron Microscope (SEM) for their uniformity and microstructure.

EXAMPLE 1

Preparation of Composite

The composites were prepared in batches of 300 grams of total material. The blending was carried out in two steps. First, solid polymer powders such as POLYOX®, PEG 8000 and other polymers (as set forth in Examples 4 and 5) for desired properties were milled in a one quart ball mill for 30 minutes. To this blend, a water solution of PEG 300 and PEG 1450 was added with additional mixing. KITCHENAID and HOBART mixers were used for blending the composites of larger size (500 to 5000 grams). The resulting wet granular blend was then extruded as described in Examples 2 and 3.

EXAMPLE 2

Air Blown Extrusion Process

A composite sample, as prepared in Example 1, was fed to a heated circular die using a single screw Brabender extruder (Model #11505). The extruder chamber was furnished with a three zone electric heating and control system. The blend was heated to about 125° C. prior to entering the circular die. With the help of air that was blowing from the center of the die, the hot extruded film was blown into a cylindrical shape. After it had cooled, the film was rolled on a take-up roller that was located about three feet from the die. The film thickness was about 0.2 mm.

EXAMPLE 3

Slot Cast Die Extrusion and Pressing Process

A wet granular mass, as prepared in Example 1, was fed to a 2" wide slot cast die using a single screw Brabender extruder (Model #11505). The extruder chamber was furnished with a three zone electric heating and control system. In the extruder chamber, the composite was heated to 125° C. before it was extruded from the die. The die body was heated to about 125° C. The thickness of the tape from the slot cast die was in the range of 1 to 2.5 mm. The tape was cooled on a moving belt and taken up on a roller. Using a CARVER® press, pieces from the extruded tape were pressed to about 0.2 mm thick films between two electrically heated plates,. This operation was carried out at about 2000 pound and 100° C. The film pieces, thus produced, were subjected to physical properties evaluation such as strength, dissolution, permeability, sealing, etc.

EXAMPLE 4

Flexible Lip Ribbon Die Extrusion

A wet granular mass, as prepared in Example 1, was fed to a electrically heated 3" flexible lip ribbon die using a single stage mixing screw Brabender Extruder (Model # PL2000-6 with Plati-Corder data processing system). The extruder chamber was furnished with a four zone electric heating and control system. The composite was fed to the extruder with the help of a single screw volumetric feeder. In the extruder chamber, the composite was heated to 120° C. before it was fed to the die. The die was heated to about 120° C. The semi-solid film from the die was picked up by a film take-off system which had three adjustable gap drums equipped with temperature monitoring and control capabilities.. After passing between the drums, the film was air cooled and rolled on a 2.5" diameter roller. The film thickness was controlled by a combination of adjustments between the die-lip gap, the drum gap, and the speed of the take-off system. The film thickness was maintained between 0.2 to 0.4 mm. Thermo-mechanical properties consisting of melt behavior and creep behavior were measured for these films using DSC (differential scanning calorimeters) TA 2920 and TMA 2940 respectively. The DSC melt curve indicated that the softening starts at about 50° C., and the melting occurs at about 62° C.

EXAMPLE 5

Alkylene Oxide Polymer Compositions a) The following films were made according to procedures described in Examples 1 and 2.

TABLE 1

Composition and Properties of Air Blown Films

| No. | Component | Quantity (wt. %) | Tensile Strength (psi) |
|---|---|---|---|
| 1. | POLYOX ® WSR N-750 | 54 | 885 |
|   | PEG Compound 20M | 27 |   |
|   | PEG 1450 | 8.0 |   |
|   | PEG 300 | 5.5 |   |
|   | Water | 5.5 |   |
| 2. | POLYOX ® WSR N-750 | 51.2 | 877 |
|   | PEG Compound 20M | 25.7 |   |
|   | PVAc (GB 101) | 5.2 |   |
|   | PEG 1450 | 7.5 |   |
|   | PEG 300 | 5.3 |   |
|   | Water | 5.1 |   |
| 3. | POLYOX ® WSR N-750 | 48.4 | 825 |
|   | PEG Compound 20M | 24.2 |   |
|   | PVAc (GB 101) | 9.6 |   |
|   | PEG 1450 | 7.5 |   |
|   | PEG 300 | 5.3 |   |
|   | Water | 5.1 |   | b) The following films were made according to procedures described in Examples 1 and 3.

TABLE 2

Composition and Properties of Extruded and Pressed Films

| No. | Component | Quantity (wt. %) | Tensile Strength (psi) |
|---|---|---|---|
| 1. | POLYOX ® WSRN-750 | 54 | 1205 |
|   | PEG 8000 | 27 |   |
|   | PEG 1450 | 8.0 |   |
|   | PEG 300 | 5.5 |   |
|   | Water | 5.5 |   |
| 2. | POLYOX ® WSR N-750 | 54 | 1120 |
|   | MPEG 5000 | 27 |   |
|   | PEG 1450 | 8.0 |   |
|   | PEG 300 | 5.5 |   |
|   | Water | 5.5 |   |
| 3. | POLYOX ® WSR N-750 | 51.4 | 796 |
|   | PEG 8000 | 25.7 |   |
|   | PEG 1450 | 7.6 |   |
|   | PEG 300 | 5.3 |   |
|   | PVAc (GB 101) | 4.76 |   |
|   | Water | 5.24 |   |
| 4. | POLYOX ® WSR N-750 | 51.4 | 1073 |
|   | PEG 8000 | 25.7 |   |
|   | PEG 1450 | 7.6 |   |
|   | PEG 300 | 5.3 |   |
|   | PVP | 4.76 |   |
|   | Water | 5.24 |   |
| 5. | POLYOX ® WSR N-750 | 51.4 | 1237 |
|   | PEG 8000 | 25.7 |   |
|   | PEG 1450 | 7.6 |   |
|   | PEG 300 | 5.3 |   |
|   | WSR N-10 | 4.76 |   |
|   | Water | 5.24 |   |
| 6. | POLYOX ® WSR N-750 | 51.4 | 1235 |
|   | PEG 8000 | 25.7 |   |
|   | PEG 1450 | 7.6 |   |
|   | PEG 300 | 5.3 |   |
|   | PCL 161 | 4.76 |   |
|   | Water | 5.24 |   |
| 7. | POLYOX ® WSR N-750 | 51.4 | 1139 |
|   | PEG 8000 | 25.7 |   |
|   | PEG 1450 | 7.6 |   |
|   | PEG 300 | 5.3 |   |
|   | HEC QP-40 | 4.76 |   |
|   | Water | 5.24 |   |

A 0.2 mm thick film of all polymer blends in Tables 1 and 2 above dissolved in 100% water within 2 to 10 minutes, however, they were insoluble in PEG 400 containing 0 to 25 wt.% water. They dissolved in aqueous PEG 400 solution containing 50% or more water, but, the dissolution rate was significantly slower than in 100% water and depended on water concentration in the solution.

Comparative Examples

The following compositions were prepared according to Example 1 but were not readily extrudable or incapable of being extruded or otherwise provided undesirable properties.

TABLE 3

| No. | Component | Quantity (wt. %) | Observations |
|---|---|---|---|
| 1. | POLYOX ® WSR N-750 | 6.3 | Paste like |
|   | PEG Compound 20M | 33.1 |   |
|   | PEG 400 | 55.0 |   |
|   | Water | 5.0 |   |
| 2. | POLYOX ® WSR N-3000 | 92 | tough will not mold or press |
|   | PEG Compound 20M | 3 |   |
|   | PEG 1450 | 1.8 |   |
|   | PEG 300 | 1.2 |   |
|   | Water | 2 |   |
| 3. | POLYOX ® WSR N-750 | 5.2 | brittle, low strength |
|   | PEG 8000 | 75.8 |   |
|   | PEG 1450 | 6.2 |   |
|   | PEG 300 | 4.3 |   |
|   | Water | 8.5 |   |
| 4. | POLYOX ® WSR N-750 | 31.8 | extremely tacky |
|   | PEG Compound 20M | 31.8 |   |
|   | PEG 400 | 31.8 |   |
|   | Water | 4.6 |   |

TABLE 3-continued

| No. | Component | Quantity (wt. %) | Observations |
|---|---|---|---|
| 5. | POLYOX ® WSR N-3000 | 90 | difficult to mold or press |
|  | PEG Compound 20M | 5 |  |
|  | PEG 1450 | 1.8 |  |
|  | PEG 300 | 1.2 |  |
|  | Water | 2 |  |
| 6. | POLYOX ® WSR N-750 | 25 | brittle, low strength |
|  | PEG 8000 | 60 |  |
|  | PEG 1450 | 7.6 |  |
|  | PEG 300 | 5.3 |  |
|  | Water | 2.1 |  |

FLEXIBLE LIP RIBBON DIE EXTRUDED FILMS

The following films were made according to Examples 1 and 4.

TABLE 4

Composition Properties of Flexible Lip Die Extruded Films

| No. | Component | Quantity (wt. %) | Elongation (% at 25° C.) | Tensile Strength (psi) |
|---|---|---|---|---|
| 1. | POLYOX ® WSR N-750 | 54 | 200 | 994 |
|  | PEG 8000 | 27 |  |  |
|  | PEG 1450 | 8.0 |  |  |
|  | PEG 300 | 5.6 |  |  |
|  | Water | 5.4 |  |  |
| 2. | POLYOX ® WSR N-750 | 54 | 650 | 935 |
|  | MPEG 5000 | 27 |  |  |
|  | PEG 1450 | 8.0 |  |  |
|  | PEG 300 | 5.6 |  |  |
|  | Water | 5.4 |  |  |
| 3. | POLYOX ® WSR N-750 | 49 | 700 | 993 |
|  | MPEG 5000 | 32 |  |  |
|  | PEG 1450 | 8.0 |  |  |
|  | PEG 300 | 5.6 |  |  |
|  | Water | 5.4 |  |  |
| 4. | POLYOX ® WSR N-750 | 44 | 350 | 1498 |
|  | MPEG 5000 | 37 |  |  |
|  | PEG 1450 | 8.0 |  |  |
|  | PEG 300 | 5.6 |  |  |
|  | Water | 5.4 |  |  |
| 5. | POLYOX ® WSR N-750 | 49.0 | 250 | 972 |
|  | MPEG 5000 | 27.0 |  |  |
|  | MPEG 2000 | 5.0 |  |  |
|  | PEG 1450 | 8.0 |  |  |
|  | PEG 300 | 5.6 |  |  |
|  | Water | 5.4 |  |  |
| 6. | POLYOX ® WSR N-750 | 51.3 | 400 | 1127 |
|  | MPEG 5000 | 26.5 |  |  |
|  | PVAc (GB 101) | 5.0 |  |  |
|  | PEG 1450 | 7.6 |  |  |
|  | PEG 300 | 5.3 |  |  |
|  | Water | 5.2 |  |  |
| 7. | POLYOX ® WSR N-750 | 54.0 | 300 | 953 |
|  | PEG 8000 | 17.0 |  |  |
|  | PEG 3350 | 10.0 |  |  |
|  | PEG 1450 | 8.0 |  |  |
|  | PEG 300 | 5.6 |  |  |
|  | Water | 5.4 |  |  |
| 8. | POLYOX ® WSR N-750 | 38.0 | 100 | 830 |
|  | PEG 8000 | 38.0 |  |  |
|  | POLYOX ® WSR N-1105 | 5.0 |  |  |
|  | PEG 1450 | 8.0 |  |  |
|  | PEG 300 | 5.6 |  |  |
|  | Water | 5.4 |  |  |

In addition to the specific aspects of the invention described above, those skilled in the art will recognize that other aspects of the invention are intended to be included within the scope of the claims which follow. For example, the alkylene oxide polymer compositions of the present invention may comprise other ingredients, monomers and polymers in addition to those specifically described herein. Also, the compositions of the present invention may have utility for other uses than those specifically described herein.

We claim:

1. An alkylene oxide polymer composition characterized in that said polymer composition has a molecular weight distribution as follows:
    (a) from about 1 to 19 weight percent based on the total composition of a polymer fraction having a number average molecular weight of from about 100 to 2000 g/gmol;
    (b) from about 10 to 60 weight percent based on the total composition of a polymer fraction having a number average molecular weight of from about 1000 to 50,000 g/gmol;
    (c) from about 25 to 89 weight percent based on the total composition of a polymer fraction having a weight average molecular weight of from about 50,000 to 10,000 g/gmol;
    with the proviso that polymer fraction (a) and polymer fraction (b) do not have the same molecular weight.

2. The composition of claim 1 wherein from about 2 to 18 weight percent based on the total composition has a number average molecular weight of from about 100 to 1000 g/gmol.

3. The composition of claim 1 wherein from about 20 to 55 weight percent based on the total composition has a number average molecular weight of from about 1000 to 30,000 g/gmol.

4. The composition of claim 1 wherein from about 35 to 70 weight percent based on the total composition has a weight average molecular weight of from about 100,000 to 4,000,000 g/gmol.

5. The composition of claim 1 wherein further comprising from about 1 to 10 weight percent water.

6. The composition of claim 1 further comprising at least one other synthetic or naturally occurring polymer.

7. The composition of claim 6 wherein the other polymer is selected from the group consisting of polysaccharides and derivatives thereof, polyvinyl pyrrolidones, polycaprolactones, polyvinyl acetates polycarboxylic acids and mixtures thereof.

8. The composition of claim 1 in the form of particles, granules, extrudates, tablets or capsules.

9. The composition of claim 1 in form of a film.

10. The composition of claim 1 which is substantially insoluble in aqueous solution of polyethylene glycol having a number average molecular weight of about 400 g/gmol comprising about 25 weight percent water or less.

11. A capsule comprising:
    (i) a continuous wall having an outer surface and an inner surface, said wall comprised of an alkylene oxide polymer composition having a molecular weight distribution as follows;
    (a) from about 1 to 19 weight percent based on the total composition of a polymer fraction having a number average molecular weight of from about 100 to 2000 g/gmol;
    (b) from about 10 to 60 weight percent based on the total composition of a polymer fraction having a number average molecular weight of from about 1000 to 50,000 g/gmol;
    (c) from about 25 to 89 weight percent based on the total composition of a polymer fraction having a weight average molecular weight of from about 50,000 to 10,000 g/gmol;
with the proviso that polymer fraction (a) and polymer fraction (b) do not have the same molecular weight; and
(ii) an inner space at least partially surrounded by said inner surface.

12. The capsule of claim 11 wherein said polymer composition further comprises from about 1 to 10 weight percent water based on the total composition.

13. The capsule of claim 11 wherein said inner space comprises a liquid.

14. The capsule of claim 13 wherein said liquid comprises a physiologically acceptable carrier.

15. The capsule of claim 14 wherein said liquid comprises an aqueous solution of a polyalkylene glycol.

16. The capsule of claim 15 wherein the aqueous solution comprises about 25 weight percent water or less.

* * * * *